US010458231B2

(12) United States Patent
Nguyen et al.

(10) Patent No.: US 10,458,231 B2
(45) Date of Patent: Oct. 29, 2019

(54) ESTIMATING IN SITU STRESS FROM ACOUSTIC EMISSION SOURCE PARAMETERS

(71) Applicant: Halliburton Energy Services, Inc., Houston, TX (US)

(72) Inventors: Philip D. Nguyen, Houston, TX (US); Jesse Clay Hampton, Conroe, TX (US); Douglas Everett Wyatt, Kingwood, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 398 days.

(21) Appl. No.: 15/515,542

(22) PCT Filed: Oct. 31, 2014

(86) PCT No.: PCT/US2014/063447
§ 371 (c)(1),
(2) Date: Mar. 29, 2017

(87) PCT Pub. No.: WO2016/068998
PCT Pub. Date: May 6, 2016

(65) Prior Publication Data
US 2017/0218753 A1 Aug. 3, 2017

(51) Int. Cl.
*E21B 49/00* (2006.01)
*G01N 29/14* (2006.01)
(Continued)

(52) U.S. Cl.
CPC ............ *E21B 49/006* (2013.01); *E21B 43/26* (2013.01); *E21B 49/00* (2013.01); *G01N 29/14* (2013.01);
(Continued)

(58) Field of Classification Search
CPC ......... E21B 43/26; E21B 49/00; G01N 29/14; G01N 29/4472
(Continued)

(56) References Cited

U.S. PATENT DOCUMENTS 8,600,716 B2 * 12/2013 Bradford .................. G01V 1/30
367/25
2009/0010104 A1 1/2009 Leaney
(Continued)

OTHER PUBLICATIONS

International Search Report and Written Opinion of PCT Application No. PCT/US2014/063447 dated Jul. 16, 2015: pp. 1-15.

*Primary Examiner* — Edward Raymond
(74) *Attorney, Agent, or Firm* — Chamberlain Hrdlicka (57) ABSTRACT

A method can include receiving acoustic emission data for acoustic emissions originating in a formation, performing a moment tensor analysis of the data, thereby yielding acoustic emission source parameters, determining at least one acoustic emission source parameter angle having a highest number of associated acoustic emission events, and calculating an in situ stress parameter, based on the acoustic emission source parameter angle. A system can include multiple sensors that sense acoustic emissions originating in a formation, and a computer including a computer readable medium having instructions that cause a processor to perform a moment tensor analysis of the data and yield acoustic emission source parameters, determine at least one acoustic emission source parameter angle having a highest number of associated acoustic emission events, and calculate an in situ stress parameter, based on the acoustic emission source parameter angle.

21 Claims, 5 Drawing Sheets

(51) Int. Cl.
*G01N 29/44* (2006.01)
*G01V 1/28* (2006.01)
*E21B 43/26* (2006.01)

(52) U.S. Cl.
CPC ......... *G01N 29/4472* (2013.01); *G01V 1/284* (2013.01); *G01V 1/288* (2013.01); *G01V 2210/123* (2013.01); *G01V 2210/1234* (2013.01); *G01V 2210/65* (2013.01)

(58) Field of Classification Search
USPC ............................... 702/11, 13, 14, 182–185
See application file for complete search history.

(56) References Cited

U.S. PATENT DOCUMENTS

| | | |
|---|---|---|
| 2009/0048783 A1 | 2/2009 | Jechumtalova et al. |
| 2009/0299637 A1 | 12/2009 | Dasgupta |
| 2012/0318500 A1 | 12/2012 | Urbancic et al. |
| 2014/0052377 A1 | 2/2014 | Downie |
| 2014/0188447 A1 | 7/2014 | Venkataraman et al. |

\* cited by examiner

FIG. 5

ESTIMATING IN SITU STRESS FROM ACOUSTIC EMISSION SOURCE PARAMETERS

TECHNICAL FIELD

This disclosure relates generally to systems and methods utilized in conjunction with a subterranean well and, in one example described below, more particularly provides for estimating in situ stress from acoustic emission source parameters.

BACKGROUND

Propagation of fractures or cracks in an earth formation is influenced heavily by a stress regime in the formation. It is, therefore, advantageous to be able to determine or estimate in situ stress in the formation, including principal stress magnitudes, principal stress ratio and principal angle. It will, thus, be readily appreciated that advancements in this art are continually needed.

DETAILED DESCRIPTION

Figure 1:
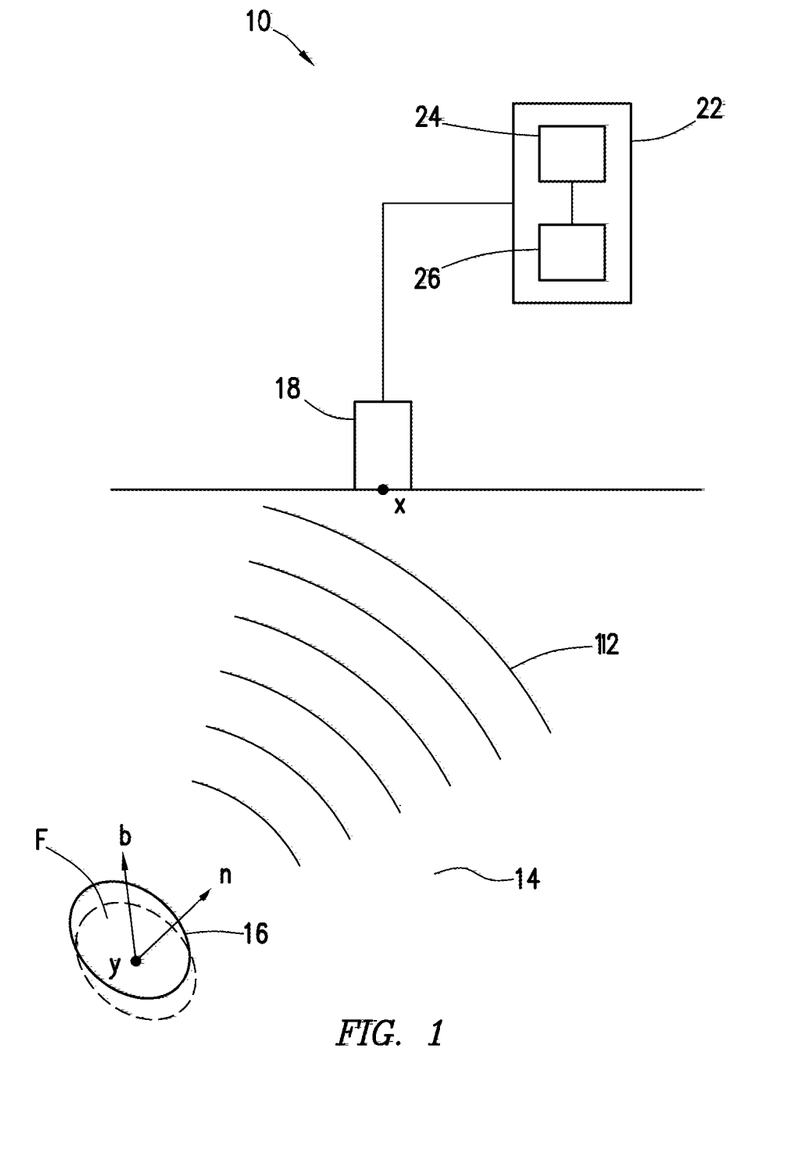
FIG. 1 is a representative partially cross-sectional view of a well system and associated method which can embody principles of this disclosure.

Representatively illustrated in FIG. 1 is an in situ stress determination system 10, and an associated method, which system and method can embody principles of this disclosure. However, it should be clearly understood that the system 10 and method are merely one example of an application of the principles of this disclosure in practice, and a wide variety of other examples are possible. Therefore, the scope of this disclosure is not limited at all to the details of the system 10 and method described herein and/or depicted in the drawings.

As described more fully below, the method provides for determining in situ stress ratios between maximum and minimum principal stresses, as well as orientations and directions of these stresses from acoustic emission (AE) source parameters. A validation of in situ stress directions is provided from acoustic emission moment tensor analysis source parameters.

An in situ stress ratio (maximum principal stress divided by minimum principal stress) is provided. No previous knowledge of in situ conditions is required. A determination can be made, with only enough acoustic emission data for moment tensor analysis. The method also provides information as to whether an area of interest is in a tectonically stressed environment.

Micro-fractures 16 can be monitored by detecting sound waves, or acoustic emissions 12, that are produced during a fracturing process. As used herein, the term "acoustic emissions" indicates localized and irreversible releases of stress energy.

Typically, the release of stress energy in the form of an elastic wave is due to permanent damage caused within a source material, such as an earth formation 14. For example, the permanent damage may be in the form of crack growth or bond delamination. Acoustic emissions 12 can be used for deconvolution of tensile, shear and mixed mode events via use of moment tensor analysis of the type well known to those skilled in the art.

FIG. 1 representatively illustrates nucleation of a fracture surface F at point y. In the FIG. 1 example, crack displacement with acoustic emission source parameters is depicted.

In FIG. 1, n represents a normal vector of an internal fracturing plane. b represents a displacement discontinuity vector (also referenced in geophysics literature as L).

As will be understood by those skilled in the art, the displacement discontinuity vector b being parallel to the normal vector n represents a tensile case. Conversely, the displacement discontinuity vector b and the normal vector n being separated by 90 degrees represents pure shear fracturing.

This simplifies crack kinematics into two direction vectors b, n representing the crack displacement vector and crack normal vector. The physical quantity of the two orientations of a crack is represented by a tensor.

In order to classify crack types from the seismic moment tensor, a unified decomposition of eigenvalues takes place. The decomposition is based on proportions of a double-couple part, a compensated linear vector dipole part, and an isotropic part.

From this, acoustic emission sources can be classified into a shear crack, tensile crack or mixed mode crack. Eigenvector information can also be obtained from the moment tensor representing the crack opening and crack slip directions.

In the FIG. 1 example, the acoustic emissions 12 are sensed by a sensor 18 positioned at point x on the earth's surface. Although only one sensor 18 is depicted in FIG. 1, multiple sensors would typically be used, with the number being sufficient to generate acoustic data for moment tensor analysis.

Note that it is not necessary for the sensors 18 to be positioned on the earth's surface. In another example representatively illustrated in FIG. 2, multiple sensors 18 are distributed longitudinally along a wellbore 20 drilled into the formation 14. In the FIG. 2 example, a depicted section of the wellbore 20 is uncased or open hole, but in other examples the sensors 18 could be positioned in a cased or lined section of the wellbore.

Figure 2:
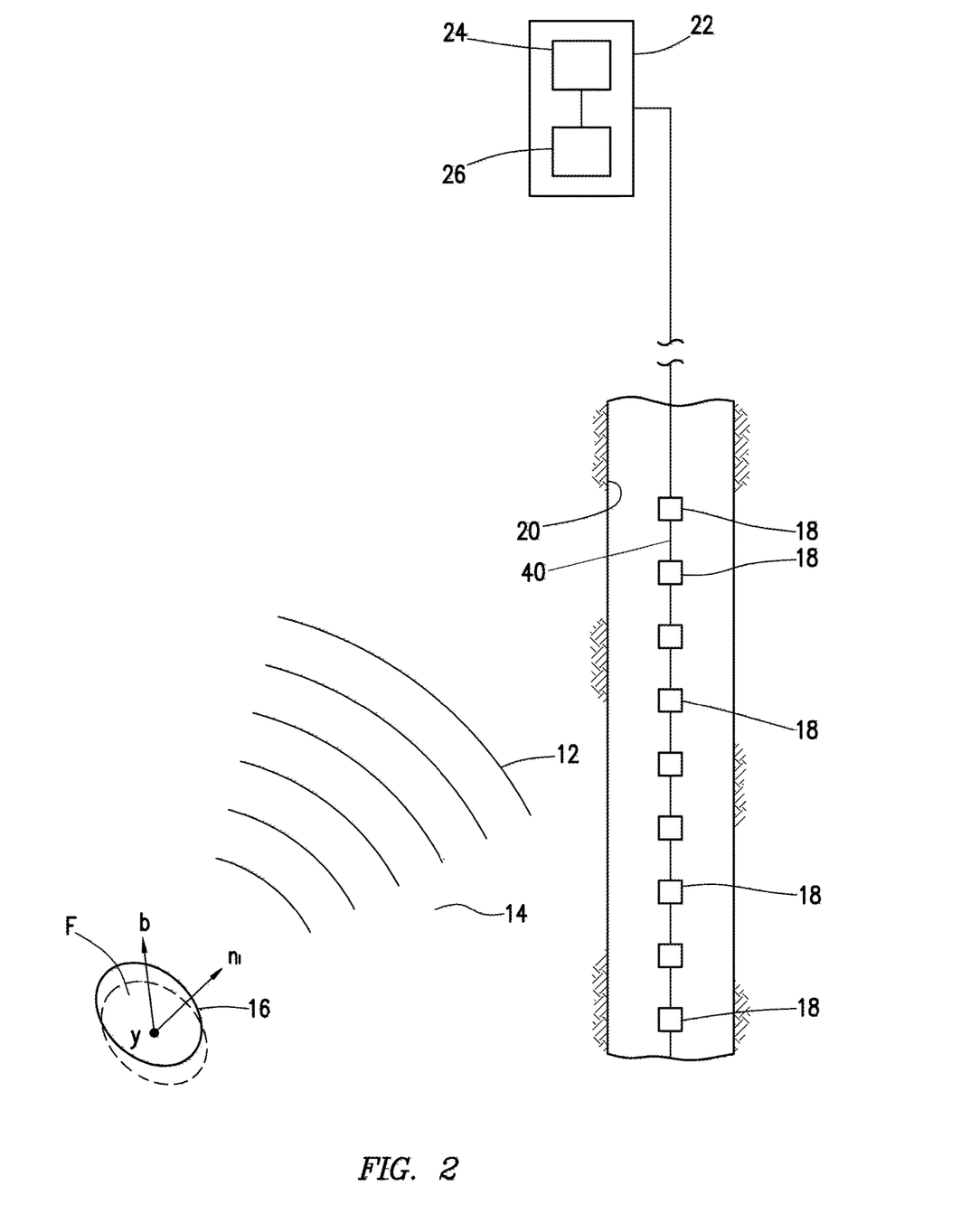
FIG. 2 is a representative partially cross-sectional view of another example of the system and method.

The sensors 18 may be conveyed into the wellbore 20 with a conveyance 40. For example, a wireline, slickline, coiled tubing, drill string, tubing string, tractor or other type of conveyance may be used to convey the sensors 18 into the wellbore 20.

The sensors 18 in the FIGS. 1 & 2 examples are connected (e.g., via wired or wireless telemetry) to a receiver or computer 22. The computer 22 is used to record and process acoustic emission data received from the sensors 18.

The computer 22 in this example includes at least a processor 24 and memory 26. The processor 24 receives acoustic emission data from the sensors 18 and manipulates/processes that data. The memory 26 stores instructions for operation of the processor 24, and stores raw and processed data. The memory 26 can be a computer readable medium, such as volatile or non-volatile memory, magnetic media, optical media, etc.

The processor 24 and memory 26 can perform additional or different functions in keeping with the scope of this disclosure. In other examples, different types of computers may be used, and the computer 22 could include other equipment (such as, input and output devices, etc.). Thus, the scope of this disclosure is not limited to use of any particular type or construction of computer 22 or sensors 18.

Figure 3:
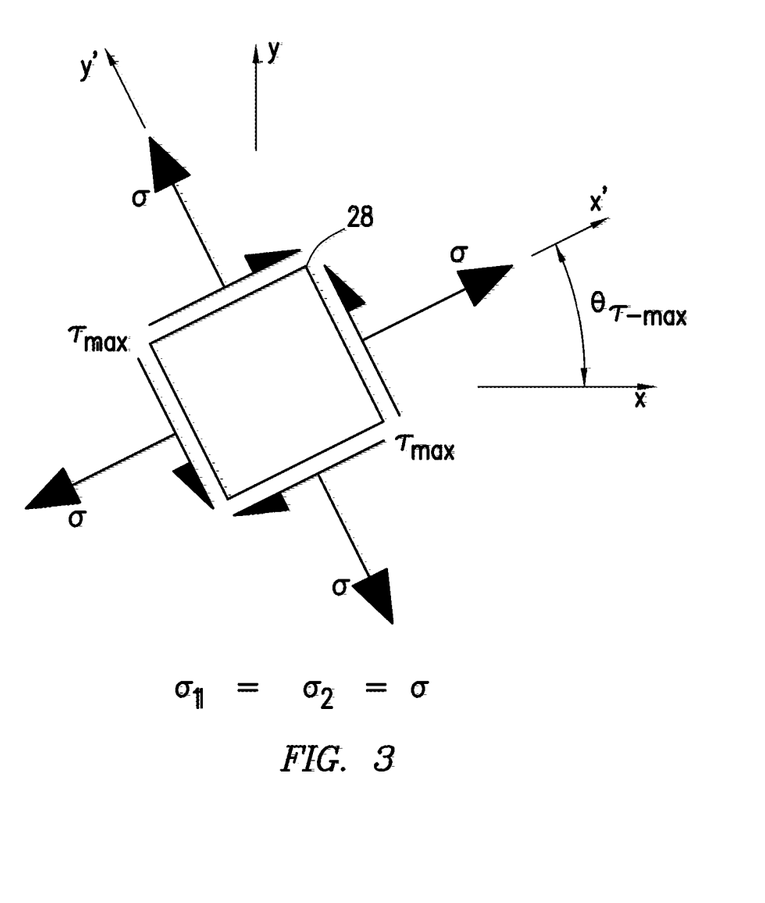
FIG. 3 is a representative view of a rock element, showing stresses acting on the rock element, and orientations and directions of the stresses.

Referring additionally now to FIG. 3, an infinitesimal rock element 28 under true tri-axial stress σ is representatively illustrated. In situ, rock in the earth formation 14 (see FIGS. 1 & 2) is under tri-axial confinement.

Due to magnitudes of principal stresses $\sigma_1$, $\sigma_2$, an angle of maximum shear stress $\theta_{\tau\text{-}max}$ exists. In this example, the principal stresses are equal ($\sigma_1 = \sigma_2 = \sigma$).

The maximum shear stress angle $\theta_{\tau\text{-}max}$ is offset from the horizontal X-axis. This angle of maximum shear stress $\theta_{\tau\text{-}max}$ is a most likely orientation of shear fracture development in the formation 14 in an absence of artificial discontinuities.

Using information gained from the acoustic emissions 12 associated with micro-fractures 16 (see FIGS. 1 & 2), moment tensor analysis is performed, in order to obtain a crack displacement vector b and a crack face normal vector n. The orientations and directions of these vectors b, n are plotted to determine a highest number of events with a similar angle from either the x, y or z axis in a Cartesian coordinate system (although other coordinate systems, such as radial, may be used if desired).

Figure 4:
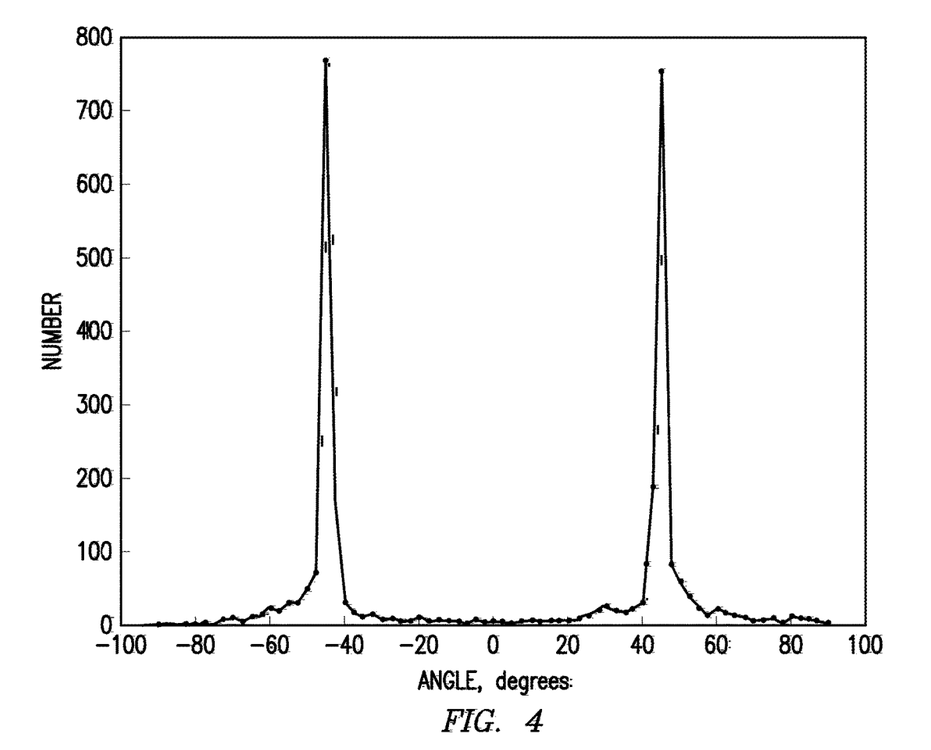
FIG. 4 is a representative example of a histogram plotting number of acoustic emission events versus displacement vector orientation.

Referring additionally now to FIG. 4, an example of a histogram of an angle between each of the acoustic emission event displacement vectors (crack motion vectors) b and the depth axis z is representatively illustrated. The FIG. 4 histogram shows large spikes at −45 and +45 degrees.

Using this information (the displacement vector b being oriented at −45 and +45 degrees) and equations 1 through 4 below, a principal stress ratio can be determined, as well as the principal stress directions:

$$\tan 2\theta_p = \frac{2\tau_{xy}}{\sigma_x - \sigma_y} \quad (1)$$

$$\sigma_{1,2} = \frac{\sigma_x + \sigma_y}{2} \pm \sqrt{\left(\frac{\sigma_x - \sigma_y}{2}\right)^2 + \tau_{xy}^2} \quad (2)$$

$$\tau_{max} = \sqrt{\left(\frac{\sigma_x - \sigma_y}{2}\right)^2 + \tau_{xy}^2} = \frac{\sigma_1 - \sigma_2}{2} \quad (3)$$

$$\tan 2\theta_s = -\frac{\sigma_x - \sigma_y}{2\tau_{xy}} \quad (4)$$

in which $\theta_p$ is the principal angle, $\tau_{xy}$ is shear stress, $\sigma_x$ is normal stress along the x axis, $\sigma_y$ is normal stress along the y axis, $\tau_{max}$ is maximum shear stress, and $\theta_s$ is shear angle. Accordingly, $$\theta_s = \theta_p +/- 45° \quad (5).$$

Taking the predominant angles (−45 and +45 degrees in the FIG. 4 example), the system of Equations 1-4 above can be solved in reverse order (that is, starting with Equation 4 and working backward). Thus, using the predominant angles, a stress ratio $\sigma_{max}/\sigma_{min}$ can be determined. Knowing a depth of the micro-fracture 16, and assuming a vertical stress of ~1 psi (pounds per square foot) per foot of depth (approximately 21 Pa/m), the principle stresses can be deconvolved from the stress ratio $\sigma_{max}/\sigma_{min}$.

Figure 5:
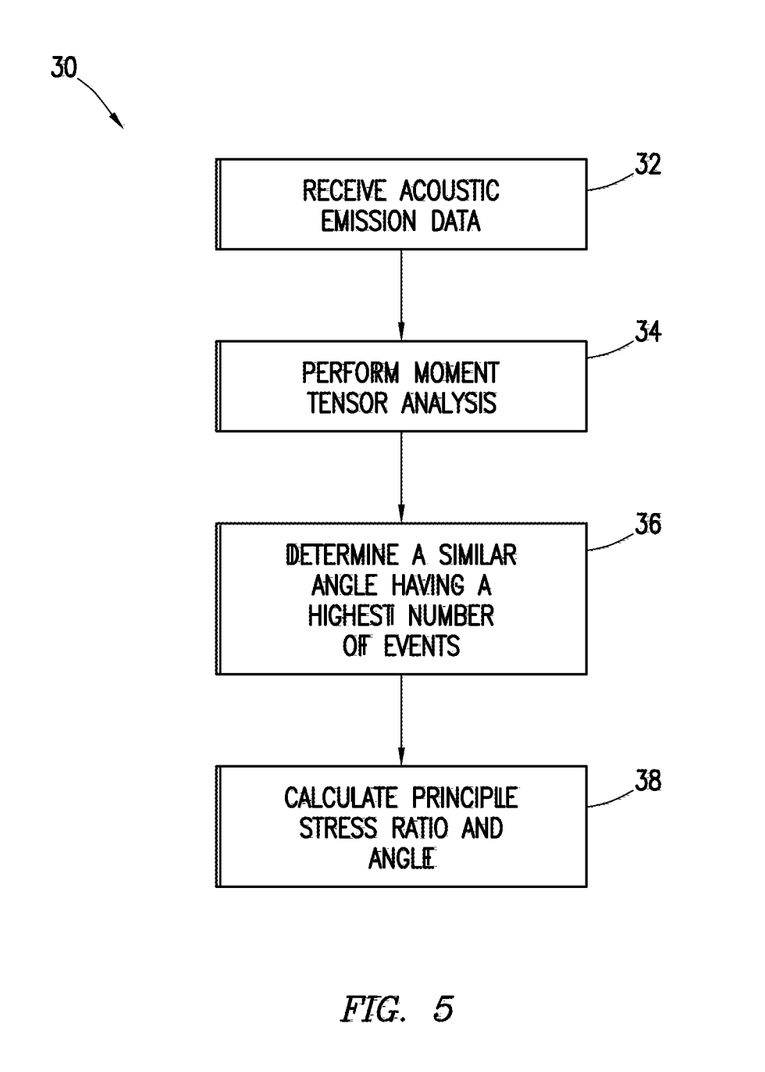
FIG. 5 is a representative flowchart for one example of the method.

Referring additionally now to FIG. 5, a representative flowchart for one example of the method 30 is representatively illustrated. The method 30 as depicted in FIG. 5 results in a calculation of principal stress ratio and angle $\theta_p$, but the scope of this disclosure is not limited to calculation of any particular parameter or combination of parameters. The method 30 may be performed with the system 10 described above, or the method may be performed with other systems.

In step 32, acoustic emission data is received. In the FIGS. 1 & 2 examples, the sensors 18 sense the acoustic emissions 12 and transmit data indicative of those acoustic emissions to the receiver or computer 22.

In step 34, a moment tensor analysis is performed. The moment tensor analysis yields the displacement vector b and the normal vector n. Moment tensor analysis is well known to those skilled in the art (e.g., see Microseismic Moment Tensors—A path to understanding frac growth, A. Berg and T. Urbancic, The Leading Edge, March 2010, v. 29, p. 320-324), and so such analysis is not described further herein.

In step 36, a similar angle having a highest number of acoustic emission events is determined. In the FIG. 4 example described above, a histogram is plotted for displacement vector b angles, and the histogram indicates a highest number of acoustic emission events at angles of −45 degrees and +45 degrees.

In step 38, the principal stress ratio ($\sigma_{max}/\sigma_{min}$) and principal angle $\theta_p$ are calculated. As described above, Equations 1-4 may be used for this purpose.

In another example, a method of determining a map of fracture geometry can comprise transmitting data of elastic waves (such as acoustic emissions 12) generated during a fracturing treatment via sensors 18 installed along the wellbore 20, allowing the data to be received by the receiver or computer 22, and processing the received data. The map of fracture geometry can comprise displacement and normal vectors b, n and principal stress ratios ($\sigma_{max}/\sigma_{min}$) and angles $\theta_p$.

In another example, a method of passive monitoring, or "listening" to natural stress release and/or natural stress related motion in an open borehole can be performed by means of acoustic emission and/or other acoustic sensors 18 placed into a recently drilled wellbore 20 before any additional treatment, in order to allow acoustic data to be received by the receiver or computer 22, and processing the received data.

The method described above can determine in situ stress ratios, and orientations and directions of maximum and minimum principal stresses, using only acoustic emission source parameters, and does not require any environmental information. The method may also determine if an area of interest is in a tectonically stressed environment (indicated by a relatively large principal stress ratio).

The method utilizes only micro-fracture acoustic emission data, whether that be microseismic hydraulic fracture data, or acoustic emissions collected in an open hole wellbore, or in a mine-back experiment, or in laboratory testing for validation of principal stress directions and magnitudes. It is contemplated that any micro-fracturing that can be recorded utilizing enough sensors to perform moment tensor analysis is sufficient to determine in situ stress ratios and orientations.

It may now be fully appreciated that the above disclosure provides significant advancements to the art of in situ stress analysis. In one example described above, a method 30 of determining at least one in situ stress parameter for an earth formation 14 can comprise: receiving acoustic emission data for acoustic emissions 12 originating in the formation 14, performing a moment tensor analysis of the data, thereby yielding acoustic emission source parameters, determining at least one acoustic emission source parameter angle having a highest number of associated acoustic emission events, and calculating the in situ stress parameter, based on the acoustic emission source parameter angle.

The in situ stress parameter may comprise a principal stress ratio $\sigma_{max}/\sigma_{min}$, principal stress magnitudes $\sigma_{max}$, $\sigma_{min}$, and/or principal angle $\theta_p$.

The acoustic emission source parameters may comprise a displacement vector b and/or a normal vector n.

The method can include positioning multiple acoustic emission sensors 18 along a wellbore 20. The positioning step may include positioning the sensors 18 in an uncased section of the wellbore 20.

The sensors 18 may sense the acoustic emissions 12 prior to any fracturing operation and/or during a fracturing operation.

Also provided to the art by the above disclosure is a system 10 for determining at least one in situ stress parameter for an earth formation 14. In one example, the system 10 can comprise: multiple sensors 18 that sense acoustic emissions 12 originating in the formation 14, and a computer 22 that receives acoustic emission data from the sensors 18. The computer 22 can include a computer readable medium (e.g., memory 26) having instructions that cause a processor 24 to: a) perform a moment tensor analysis of the data and yield acoustic emission source parameters, b) determine at least one acoustic emission source parameter angle having a highest number of associated acoustic emission events, and c) calculate the in situ stress parameter, based on the acoustic emission source parameter angle.

The sensors 18 may sense the acoustic emissions 12 in an absence of any fracturing operation and/or the sensors may sense the acoustic emissions during a fracturing operation.

Although various examples have been described above, with each example having certain features, it should be understood that it is not necessary for a particular feature of one example to be used exclusively with that example. Instead, any of the features described above and/or depicted in the drawings can be combined with any of the examples, in addition to or in substitution for any of the other features of those examples. One example's features are not mutually exclusive to another example's features. Instead, the scope of this disclosure encompasses any combination of any of the features.

Although each example described above includes a certain combination of features, it should be understood that it is not necessary for all features of an example to be used. Instead, any of the features described above can be used, without any other particular feature or features also being used.

It should be understood that the various embodiments described herein may be utilized in various orientations, such as inclined, inverted, horizontal, vertical, etc., and in various configurations, without departing from the principles of this disclosure. The embodiments are described merely as examples of useful applications of the principles of the disclosure, which is not limited to any specific details of these embodiments.

The terms "including," "includes," "comprising," "comprises," and similar terms are used in a non-limiting sense in this specification. For example, if a system, method, apparatus, device, etc., is described as "including" a certain feature or element, the system, method, apparatus, device, etc., can include that feature or element, and can also include other features or elements. Similarly, the term "comprises" is considered to mean "comprises, but is not limited to."

Of course, a person skilled in the art would, upon a careful consideration of the above description of representative embodiments of the disclosure, readily appreciate that many modifications, additions, substitutions, deletions, and other changes may be made to the specific embodiments, and such changes are contemplated by the principles of this disclosure. For example, structures disclosed as being separately formed can, in other examples, be integrally formed and vice versa. Accordingly, the foregoing detailed description is to be clearly understood as being given by way of illustration and example only, the spirit and scope of the invention being limited solely by the appended claims and their equivalents.

What is claimed is:

1. A method of determining at least one in situ stress parameter for an earth formation, the method comprising:
    receiving acoustic emission data for acoustic emissions originating in the formation;
    performing a moment tensor analysis of the data, thereby yielding acoustic emission source parameters;
    determining at least one acoustic emission source parameter angle having a highest number of associated acoustic emission events; and
    calculating the in situ stress parameter, based on the acoustic emission source parameter angle.

2. The method of claim 1, wherein the in situ stress parameter comprises a principal stress ratio.

3. The method of claim 1, wherein the at least one in situ stress parameter comprises principal stress magnitudes.

4. The method of claim 1, wherein the in situ stress parameter comprises a principal angle.

5. The method of claim 1, wherein the acoustic emission source parameters comprise a displacement vector.

6. The method of claim 1, wherein the acoustic emission source parameters comprise a normal vector.

7. The method of claim 1, further comprising positioning multiple acoustic emission sensors along a wellbore.

8. The method of claim 7, wherein the positioning further comprises positioning the sensors in an uncased section of the wellbore.

9. The method of claim 7, wherein the sensors sense the acoustic emissions prior to any fracturing operation.

10. The method of claim 7, wherein the positioning further comprises conveying the sensors into the wellbore with a conveyance.

11. The method of claim 1, wherein a sensor senses the acoustic emissions during a fracturing operation.

12. A system for determining at least one in situ stress parameter for an earth formation, the system comprising:
    multiple sensors that sense acoustic emissions originating in the formation; and
    a computer that receives acoustic emission data from the sensors, the computer including a computer readable medium having instructions that cause a processor to: a) perform a moment tensor analysis of the data and yield acoustic emission source parameters, b) determine at least one acoustic emission source parameter angle having a highest number of associated acoustic emission events, and c) calculate the in situ stress parameter, based on the acoustic emission source parameter angle.

13. The system of claim 12, wherein the in situ stress parameter comprises a principal stress ratio.

14. The system of claim 12, wherein the at least one in situ stress parameter comprises principal stress magnitudes.

15. The system of claim 12, wherein the in situ stress parameter comprises a principal angle.

16. The system of claim 12, wherein the acoustic emission source parameters comprise a displacement vector.

17. The system of claim 12, wherein the acoustic emission source parameters comprise a normal vector.

18. The system of claim 12, wherein the acoustic emission sensors are distributed along a wellbore.

19. The system of claim 18, wherein the sensors are positioned in an uncased section of the wellbore.

20. The system of claim 18, wherein the sensors sense the acoustic emissions in an absence of any fracturing operation.

21. The system of claim 12, wherein the sensors sense the acoustic emissions during a fracturing operation.

\* \* \* \* \*